(12) United States Patent
Holm

(10) Patent No.: US 6,279,399 B1
(45) Date of Patent: Aug. 28, 2001

(54) MULTI-DIMENSIONAL TRANSDUCER ARRAY APPARATUS

(75) Inventor: Sverre Holm, Asker (NO)

(73) Assignee: Vingmed Sound A/S, Horten (NO)

( * ) Notice: Subject to any disclaimer, the term of this patent is extended or adjusted under 35 U.S.C. 154(b) by 0 days.

(21) Appl. No.: 09/128,278

(22) Filed: Aug. 3, 1998

(51) Int. Cl.$^7$ ................................................ G01N 29/00
(52) U.S. Cl. .................................. 73/626; 73/628
(58) Field of Search .................. 73/626, 625, 628, 73/623, 597, 602; 367/7, 8, 11, 103, 105; 600/440, 441, 443, 444, 445, 447, 459, 463; 128/916

(56) References Cited

U.S. PATENT DOCUMENTS

| | | | |
|---|---|---|---|
| 4,550,606 | * 11/1985 | Drost | 73/626 |
| 4,694,434 | 9/1987 | Von Ramm et al. | 367/7 |
| 5,060,651 | * 10/1991 | Kondo et al. | 73/626 |
| 5,186,175 | * 2/1993 | Hirama et al. | 73/626 |
| 5,269,309 | * 12/1993 | Fort et al. | 73/597 |
| 5,490,512 | * 2/1996 | Kwon et al. | 128/661.01 |
| 5,537,367 | 7/1996 | Lockwood et al. | 367/87 |
| 5,546,807 | 8/1996 | Oxaal et al. | 73/606 |
| 5,677,491 | 10/1997 | Ishrak et al. | 73/641 |
| 5,787,049 | * 7/1998 | Bates | 73/626 |
| 5,842,473 | * 12/1998 | Fenster et al. | 128/660.09 |
| 5,934,288 | * 8/1999 | Avila et al. | 128/916 |
| 5,938,612 | * 8/1999 | Kline-Schoder et al. | 600/459 |

OTHER PUBLICATIONS

Steinberg, B, Prinnciples of Aperture and Array System Design, Wiley, New York, 1976, pp. 139–159.

Hendricks, W.J., "The Total Random Versus the Bin Approach for Random Arrays," IEEE Trans. Antennas and Propagation, vol. 39, No. 12, pp. 1757–1761, Dec. 1991.

Holm, et al., "Properties of the Beampattern of Weight–and Layout–Optimized Sparse Arrays," IEEE Trans. Ultrasonics, Ferroelectrics and Frequency Control, vol. 44, No. 5, pp. 983–991, Sep. 1997.

Austeng, et al., "1D and 2D Algorithmically Optimized Sparse Arrays," to be published in Proc. IEEE Trans. Ultrasonics Symposium, Toronto, Oct. 1997, pp. 1683–1686.

Lockwood, et al.,"Optimizing the Radiation Pattern of Sparse Periodic Two–Dimensional Arrays," IEEE Trans. Ultrasonics,Ferroelectrics and Frequency Control, vol. 43, No. 1, pp. 15–19,Jan. 1996.

* cited by examiner

Primary Examiner—Helen Kwok
(74) Attorney, Agent, or Firm—McAndrews, Held & Malloy, Ltd.; Christian G. Cabou

(57) ABSTRACT

An ultrasound imaging device comprising a set of bins, wherein each bin includes a set of transducer elements. Additionally, a set of mode switches or multiplexers are associated with the set of bins, wherein the set of mode switches or multiplexers configure the set of transducer elements in each bin to form either a one-dimensional array providing a two-dimensional scan mode or a two-dimensional array providing a three-dimensional scan mode.

21 Claims, 6 Drawing Sheets

MULTI-DIMENSIONAL TRANSDUCER ARRAY APPARATUS

BACKGROUND OF THE INVENTION

1. Field of the Invention

The present invention relates to the field of imaging through the use of radiant pulse-echo energy or ultrasound technology. More particularly, the present invention relates to a multi-dimensional transducer array which can be selectively operated in either a two-dimensional (2D) scan mode or three-dimensional (3D) scan mode.

2. Art Background

Generally, most transducer probes operate in accordance with essentially the same principle, wherein a burst or pulse of energy is introduced into the object being examined, and a return echo is received, from which an image is generated. In order to allow for different dimensional views or perspectives of a particular object/area, however, a multitude of different devices have been developed.

Currently, imaging devices are capable of providing two-dimensional (2D) or three-dimensional (3D) views of objects/areas through the use of radiant pulse-echo energy or ultrasound technology. Typical ultrasound devices, however, utilize a series of different transducer arrays contained in a variety of different probe tips which are specifically designed to obtain either a two-dimensional (2D) or three-dimensional (3D) image of a particular area of interest.

Generally, a one-dimensional transducer array configuration is utilized for obtaining a two-dimensional (2D) image of a particular object or area of interest. Specifically, a one-dimensional transducer array is utilized to obtain a two-dimensional (2D) view or image (lateral and axial), which represents a cross-section of the object or area, through a corresponding scanning plane along the X and Z axes. The one-dimensional transducer array, also known as a linear array, comprises an array of rectangular transducer elements arranged into columns which form a single-dimensional linear array. Generally, two-dimensional (2D) imaging systems use electronic scanning of a linear, curved linear, or phased array type, which typically employ 64-192 transducer elements within the probe. Accordingly, the single-dimensional linear array typically provides a relatively high quality two-dimensional (2D) profile or image of the particular area of interest.

One method of obtaining a three-dimensional (3D) view or image is accomplished by the mechanical movement of the transducer array contained in the probe (electronic/mechanical probe). The electronic/mechanical probe obtains 3D imaging by the movement of a one-dimensional array (2D imaging) about the area of interest, resulting in a third scanning dimension to provide a three-dimensional (3D) view or image. An advantage of the electronic/mechanical probe is that it can be used for conventional two-dimensional (2D) imaging by simply stopping the mechanical movement of the probe into a fixed position.

Another method for obtaining a three-dimensional (3D) view or image of an object is through electronic volume scanning. Electronic volume scanning requires a two-dimensional transducer array which is utilized to obtain a three-dimensional (3D) view or image of a particular area of interest. The two-dimensional transducer array obtains a three-dimensional (3D) view or image (lateral, axial, and elevational), which represents a cross-section of the object, through a corresponding scanning plane along the X, Y, and Z axes.

The two-dimensional transducer array typically comprises a plurality of transducer elements which are arranged into a two-dimensional configuration of columns and rows, as opposed to the one-dimensional transducer array configuration of columns used in two-dimensional (2D) scanning. The columns of the two-dimensional transducer array comprise the scanning plane used to form a two-dimensional profile of the object, and the rows of the array comprise the elevational plane used for obtaining the third dimension of the object. The probe used for electronic volume scanning, however, typically requires 2000 or more elements in order to obtain a relatively high quality full electronic volume scan. Nevertheless, this type of probe is often preferable to the electronic/mechanical probe, since the volume scan probe has a potential for relatively higher volume scan rates, due in part to the lack of mechanical movement.

For reasons of economy, based upon such considerations as the number of cables, the complexity of necessary electronic support circuitry, and associated beamformer considerations, typical three-dimensional (3D) scanning is typically implemented by using various forms of sparse array configurations. Generally, sparse array configurations utilize a limited set of transducer elements from the full two-dimensional arrangement of elements of the two-dimensional array. A typical sparse array configuration could contain between 256 and 512 transducer elements which would be utilized for three-dimensional (3D) scanning. The arrangement of the transducer elements in a sparse array can be in various formats, such as, randomly selected, randomly selected within the constraints of a binned pattern, periodic patterns with different periodicity for the transmitter and receiver elements, algorithmically optimized patterns from computer optimization, or a combination of periodic and algorithmically optimized patterns. Nevertheless, the sparse array or set of elements will generally provide a reduced image quality which may be sufficient for three-dimensional (3D) imaging. However, if a two-dimensional (2D) scan is preferred utilizing such array formats, the image quality will generally be inferior to that of a state of the art two-dimensional (2D) scanner.

To obtain two-dimensional (2D) images, all of the 2000 or more elements of the two-dimensional array must be used. The use of all 2000 or more of the elements of the two-dimensional array, however, would require a large multitude of cables and channels along with increased electronic support circuits, which would greatly increase the size, complication, and the expense of such a probe using a two-dimensional array for two-dimensional (2D) scanning. Thus, in actual practice, two separate transducer probes are typically utilized in order to provide quality imaging in variant dimensions, for example, a one-dimensional array for two-dimensional (2D) images, and a two-dimensional transducer array for three-dimensional (3D) images.

Thus, prior transducers for ultrasonic imaging have fundamental shortcomings in providing a singular probe which has the capability to provide both two-dimensional (2D) or three-dimensional (3D) images of high quality within the confines of a singular transducer probe. Therefore, it would be desirable to have an imaging device which could provide relatively high quality two-dimensional (2D) or three-dimensional (3D) images of objects within a singular transducer array contained in a singular probe.

SUMMARY AND OBJECTS OF THE INVENTION

One of the objects of the present invention is to provide a singular transducer probe configured to provide high quality two-dimensional (2D) and three-dimensional (3D) images of objects.

Another object of the present invention is to provide a singular transducer probe having a two-dimensional array, wherein the two-dimensional array can be configured to provide high quality two-dimensional (2D) or three-dimensional (3D) images.

A further object of the present invention is to provide a singular transducer probe having a two-dimensional array configured to provide high quality two-dimensional (2D) or three-dimensional (3D) images without requiring a prohibitively large number of cables, channels, and switches.

These and other objects of the present invention are provided for by an ultrasound imaging device comprising a set of bins, wherein each bin includes a set of transducer elements. Additionally, a set of mode switches or multiplexers are associated with the set of bins, wherein the set of mode switches or multiplexers configure the set of transducer elements in each bin to form either a one-dimensional array providing a two-dimensional scan mode or a two-dimensional array providing a three-dimensional scan mode.

One aspect of the present invention provides for the series of transducer elements to reside in an associated transducer assembly, wherein the series of mode selection switches are integrated into the associated transducer assembly.

Another aspect of the present invention provides that each mode switch can configure the series of transducer elements in each bin to form either a one-dimensional transducer array or a two-dimensional transducer array.

BRIEF DESCRIPTION OF THE DRAWINGS

The present invention is illustrated by way of example and not by limitation in the figures of the accompanying in which like references dictate like elements and in which.

DETAILED DESCRIPTION

Figure 1:
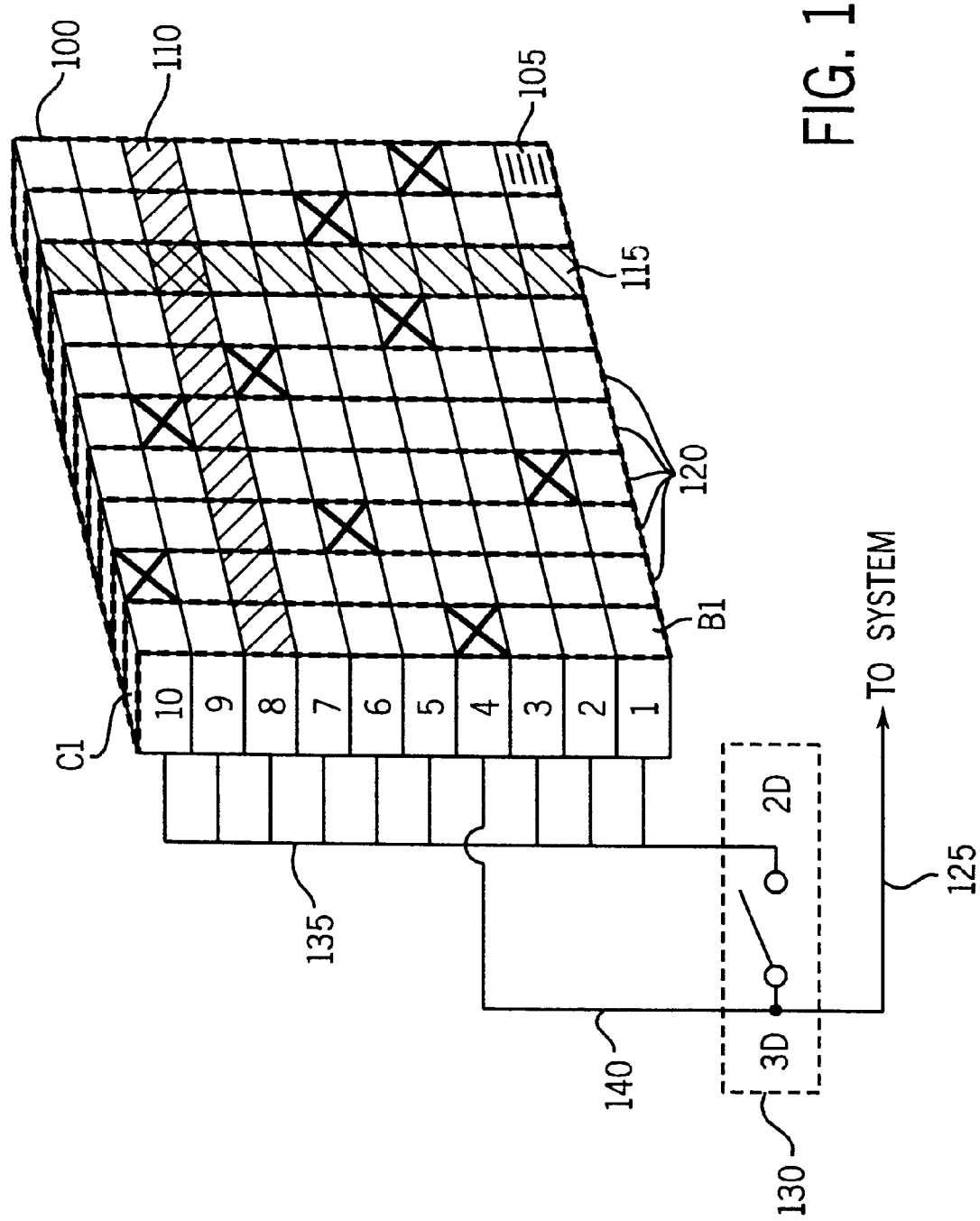
FIG. 1 is an embodiment of a two-dimensional scanning transducer array that operates in accordance with the teachings of the present invention.

The present invention provides an apparatus for generating relatively high quality two-dimensional and three-dimensional images utilizing a singular transducer probe. In the following description numerous details are set forth in order to provide a thorough understanding of the present invention. However, it will be apparent to one skilled in the art that these specific details are not required in order to practice the present invention. In other instances, well known electrical structures and circuits are not described in detail in order not to obscure the present invention unnecessarily.

As a preliminary matter, with respect to two-dimensional arrays, a brief discussion of bin configurations is provided below to aid in the understanding of the present invention.

The configuration of a two-dimensional array as related to bin size is based upon the number of elements contained within a particular array. The two-dimensional transducer array is broken down into elements in the x-direction (Nx) and elements in the y-direction (Ny) wherein the total number of elements contained in the array (Nt) is equal to the product of the elements in the x and y direction (Nt= Nx*Ny). The bin size for the array is predicated upon the number of elements (Es) which will be used in order to create a desired scanning function, such as a sparse scanning function. Therefore, the bin size (Bs) is equal to the total number of elements contained in the array (Nt) divided by the number of elements (Es) or (Nt/Es=Bs). The bin size (Bs) is determined by a bin size in both the x-direction (Nxb) and the y-direction (Nyb). Therefore, the total bin size (Bs) is equal to the product of the bin size in the x-direction (Nxb) and the bin size in the y-direction (Nyb) or (Bs=Nxb*Nyb). Further, the number of bins in the x-direction (BX) is equal to the number of elements in the x-direction (Nx) divided by the bin size in the x-direction (Nxb) or (Nx/Nxb=BX). Similarly, the number of bins in the y-direction (BY) is equal to the numer of elements in the y-direction (Ny) divided by the bin size in the x-direction (Nyb) or (Ny/Nyb=BY). The total number of bins (BT), which is equal to the number of one-dimensional elements in the present invention, is also equal to the product of the elements in the x and y direction (Nt) divided by the total bin size (Ntb) or (BT=Nt/Bs).

The aforementioned bin size calculations may be understood by example and implementation. For instance, assume that a 50×50 array having 2500 elements is being utilized. Further, assume that 250 elements from the array are to be used in order to create a desired pattern for scanning. As such, the bin size would equal 2500/250=10. Assuming a desired bin array configuration of 1×10=10, the bin size in the x-direction would be equal to 1 and the bin size in the y-direction would be equal to 10. The preferred configuration of the bins are 1xN, wherein the bin size in the x-direction would be equal to 1 and the bin size in the y-direction would be equal to N. The desired bin configuration could also have been represented as a 2×5=10 configuration if desired. Nevertheless, using the 1×10 configuration, the final number of bins in the x-direction would be fifty (50/1=50), with the final number of bins in the y-direction equal to five (50/10=5). In the 3D mode, the array operates as a sparse array with a single element connected from each bin, i.e., with a total of 250 elements.

This invention, in one embodiment, provides a method for connecting elements such that in the 2D mode, the result using the above example would be an array having 50×5 one-dimensional elements and capable of being steered along the scan direction, where there are 50 "superelements" which are described in further detail below. The remaining 5 super-elements along the elevational direction could be utilized for improved focusing above the level of conventionally available 2D transducer probes.

Having generally described how bins are configured with respect to a two-dimensional array, the present invention will be described. In one embodiment, a multi-dimensional radiant pulse-echo energy imaging device capable of generating a quality two-dimensional or a three-dimensional image utilizing a singular multi-dimensional transducer array is provided. The multi-dimensional array is typically arranged into sets of transducer elements called bins, wherein the transducer elements contained within the bins may be operated in accordance with a 2D or 3D scan mode.

One embodiment of the present invention is illustrated in FIG. 1, which illustrates a two-dimensional scanning transducer array 100. It is understood that the two-dimensional scanning transducer array 100 usually resides within an associated transducer assembly of an ultrasound probe. The two-dimensional scanning transducer array (transducer array) 100 is comprised of a series of transducer elements 105 arranged into a plurality of rows 110 and columns 115. The rows 110 and columns 115 of the transducer array 100 are configured into a series of bins 120 (1×10 bins), wherein the individual transducer elements 105 contained within each bin 120 may be selectively operated in order to allow the transducer array 100 to operate in either a 2D mode or a 3D mode. Although only a limited number of transducer elements 105 and bins 120 are shown in the figure for illustration purposes, as comprising the transducer array 100 (which is shown as a 10×10 element array comprising ten bins), additional elements 105 and bins 120 as required and/or as desired may be utilized. Moreover, the shape of the transducer elements 105 of the transducer array 100 may be configured in any desired shape so as to impart any required or desired operation to the transducer array 100.

As illustrated in FIG. 1, the transducer array 100 is comprised of a series of transducer elements 105 arranged into a plurality of rows 110 and columns 115. Each of these rows 110 and columns 115 are further configured into bins 120 which may be of any desired size or configuration in various embodiments of the present invention.

In FIG. 1, the first column C1 is configured into a bin B1 having a bin size of 1×10. The bin B1 is one element wide in the x-direction and 10 elements high in the y-direction. For ease of understanding, the remaining columns in the array 100 are likewise configured into bins of 1×10. However, the array 100 may be configured into any desired bin size of any desired size or configuration. Each bin 120 in the array 100 has a system channel 125 and an electronic mode switch 130, integrated in the transducer assembly of a probe, which are associated with a plurality of transducer elements 105 contained within the bin 120. The individual mode switch 130 operates as a multiplexer for coupling and energizing select transducer elements 105 for different scanning mode (2D and 3D) operations.

For illustrative purposes, bin B1 is discussed in some detail. However, the principles discussed in relation to bin B1 are equally applicable to one or a combination of the other bins 120 located within the transducer array 100. As illustrated, line 135 is shown coupling a series of the transducer elements 105 (i.e.—nine out of ten elements) of bin B1 in a parallel or fully connected array pattern configuration. Additionally, line 140 is shown coupled to a singular transducer element marked "X" in bin B1. Both lines 135 and 140 are shown coupled to the mode switch 130 which allows the bin B1, and thereby the transducer array 100 comprised of multiple bins 120, to be operated in either a two-dimensional (2D) mode or a three-dimensional (2D) mode.

Figure 2:
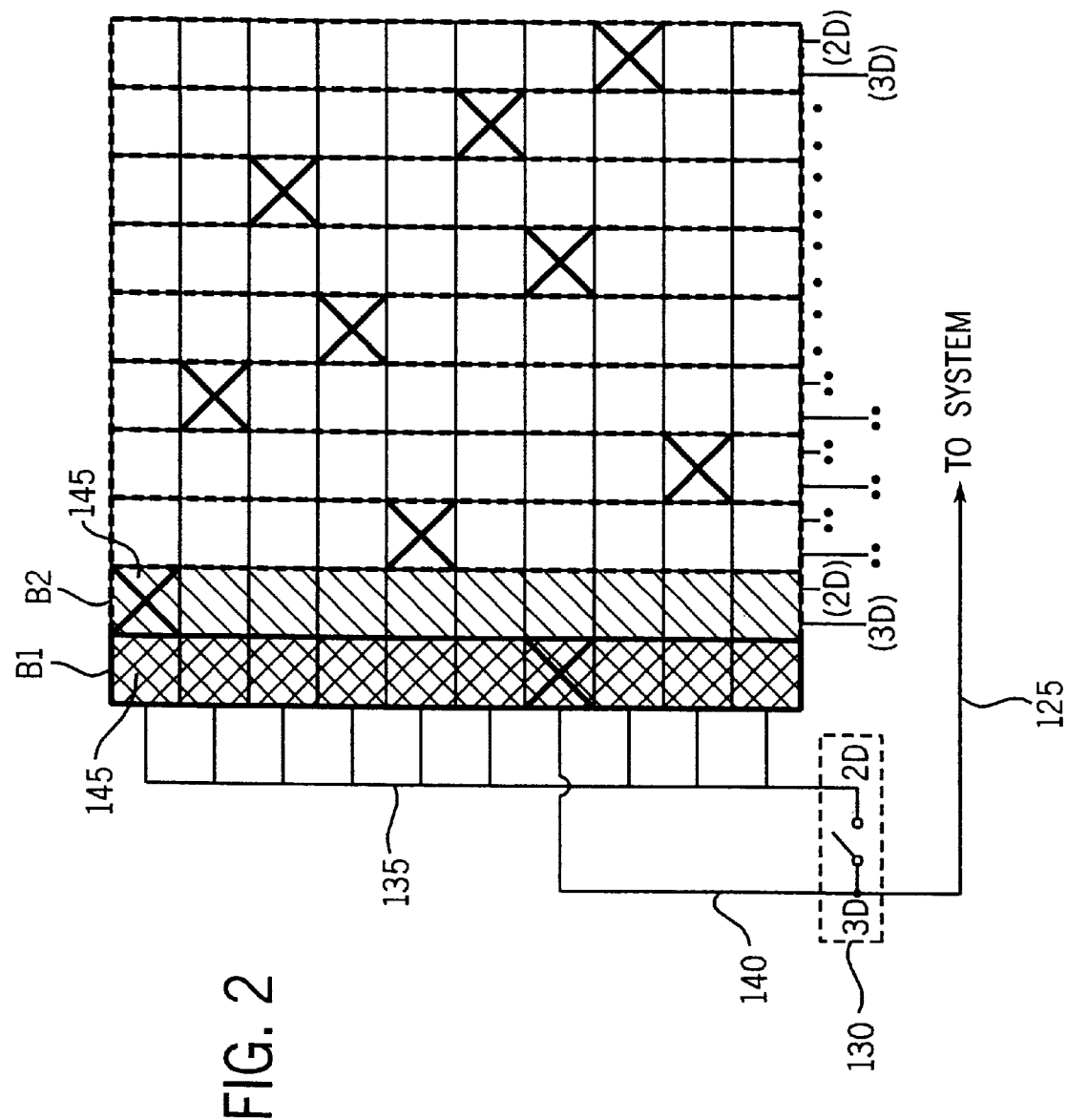
FIG. 2 is an embodiment of the two-dimensional scanning transducer array illustrating the operation of the present invention.

The operation of the transducer array 100 in relation to generating a two-dimensional (2D) image can further be explained with reference to FIG. 2. The transducer array 100 of FIG. 2 is illustrated as a 10×10 array of individual transducer element 105 configured into bin sizes of 1×10. In the two-dimensional (2D) scan mode, the transducer array 100 is constructively transformed into a series of relatively large one-dimensional scanning elements 145. The large one-dimensional scanning elements 145 allow for the generation of a quality two-dimensional (2D) image of an object. For illustrative purposes, only bin B1 will be discussed in detail. However, the principles discussed in relation to bin B1 are equally applicable to one or a combination of the other bins 120 located within the transducer array 100.

Accordingly, when the transducer array 100 is operating in the two-dimensional (2D) scan mode, the selection mode switch 130 is closed in order to allow the system to generate and receive pulses from which a two-dimensional (2D) image may be generated. Upon the closure of the selection mode switch 130, all of the elements (i.e.—elements 1–10) contained within bin B1 are constructively coupled together. As indicated previously, with respect to FIG. 1, selected transducer elements 105 contained within the bin B1 of the transducer array 100 are coupled in parallel along line 135, with line 140 being coupled to a single element in bin B1. Upon the closure of the selection mode switch 130, however, all of the transducer elements 105 coupled to each line, lines 135 and 140, are coupled in parallel forming a fully connected array pattern.

Upon the closure of the selection mode switch 130, all of the individual transducer elements 105 contained within bin B1 are activated simultaneously, thereby constructively transforming the individually parallel coupled transducers 105, contained in bin B1, into a large one-dimensional element or "'super-element" 145. Similarly, other corresponding channels and switches, represented as 3D/2D ports, for each bin 120 contained in the array 100 would likewise be activated, thereby operatively transforming the array 100, comprised of a series of individual bins 120, into a series of large one-dimensional elements or super-elements 145. For example, bin B2, adjacent to bin B1, would likewise be transformed from a bin of individual transducer elements 105 into a super-element 145 upon the closure of the respective mode switch associated with bin B2. This process is similarly carried out for each bin 120 contained within the array 100, which transforms the array 100 into a series of large one-dimensional elements or super-elements 145, thereby operatively transforming the entire array 100 into a one-dimensional array comprised of large one dimensional element or super-element 145 used for generating two-dimensional (2D) images.

As such, the configuration of the transducer array 100 allows the transducer probe to operate in either a one-dimensional transducer array configuration (2D mode) for obtaining two-dimensional (2D) images, or alternately in two-dimensional transducer array configuration (3D mode) for obtaining three-dimensional (3D) images. For a three-dimensional (3D) image, the transducer array 100 is configured to obtain a full electronic volume scan in order to generate three-dimensional (3D) images. In one embodiment, the size of the bin is one element wide along the desired 2D scan axis of the probe. Accordingly, the arrangement for switching the transducer array 100 between a two-dimensional (2D) scan mode and a three-dimensional (3D) scan mode can be accomplished via the respective mode switches 130 associated with each bin 120.

In generating a three-dimensional (3D) image, in one embodiment of the invention, the transducer array 100 is operated in a sparse array pattern in order to accomplish three-dimensional (3D) volumetric type scanning. Of particular interest, with regard to generating three-dimensional (3D) images, are the sparse binned pattern and the sparse periodic patterns.

The sparse binned pattern, also illustrated in FIG. 2, is characterized by a regular division of the transducer array 100 into equal sized bins (e.g.,: 1×10). For example, in a 50×50 element transducer array where 250 elements are to be coupled in order to create the sparse pattern, a bin size equal to the ratio of the total number of elements (50×50= 2500) and the number of connected or coupled elements (250), resulting in a bin size of 10 elements per bin [2500/ 250=10], are utilized. A bin of size 10 can be realized in two ways: either as a 2×5 elements per bin or, as shown in FIG. 2, a bin comprising 1×10 elements per bin.

Therefore, the entire transducer array 100 is divided into bins of size 1×10, with an individual active transducer element 105 (used for 3D imaging) in each bin 120 marked with an "X", with each such transducer element (X) from each of the respective bins 120 being connected to the imaging system through a respective system channel 125 for three-dimensional (3D) imaging. The individual transducer elements 105 to be connected in each bin 120, for 3D imaging, can be selected at random according to a probability density or by an algorithm which selects, for example, according to an optimization criterion.

When the transducer array 100 is operating in the 3D mode, the selection mode switch 130 is maintained in the open position in order to allow the system to generate and receive pulses from which a three-dimensional (3D) image may be generated. Upon the opening of the selection mode switch 130, one element marked "X" which is contained within bin B1 is coupled to the system. Therefore, upon the opening of the selection mode switch 130, only one transducer element in bin B1 is activated for 3D imaging in accordance with the sparse binned pattern. Similarly, other corresponding mode switches and corresponding lines, represented as 3D/2D ports, for each bin 120 may likewise be activated, thereby operatively transforming the bins 120 containing active transducer element (marked with "X") into a sparse binned pattern array for 3D imaging. For example, bin B2, adjacent to bin B1, may have an active transducer elements (marked with "X") activated for 3D imaging in accordance with the sparse binned pattern. In one embodiment, this process is similarly carried out for each bin 120 contained within the array 100, which transforms the array 100 into a sparse binned pattern array for generating three-dimensional (3D) images.

Figure 3:
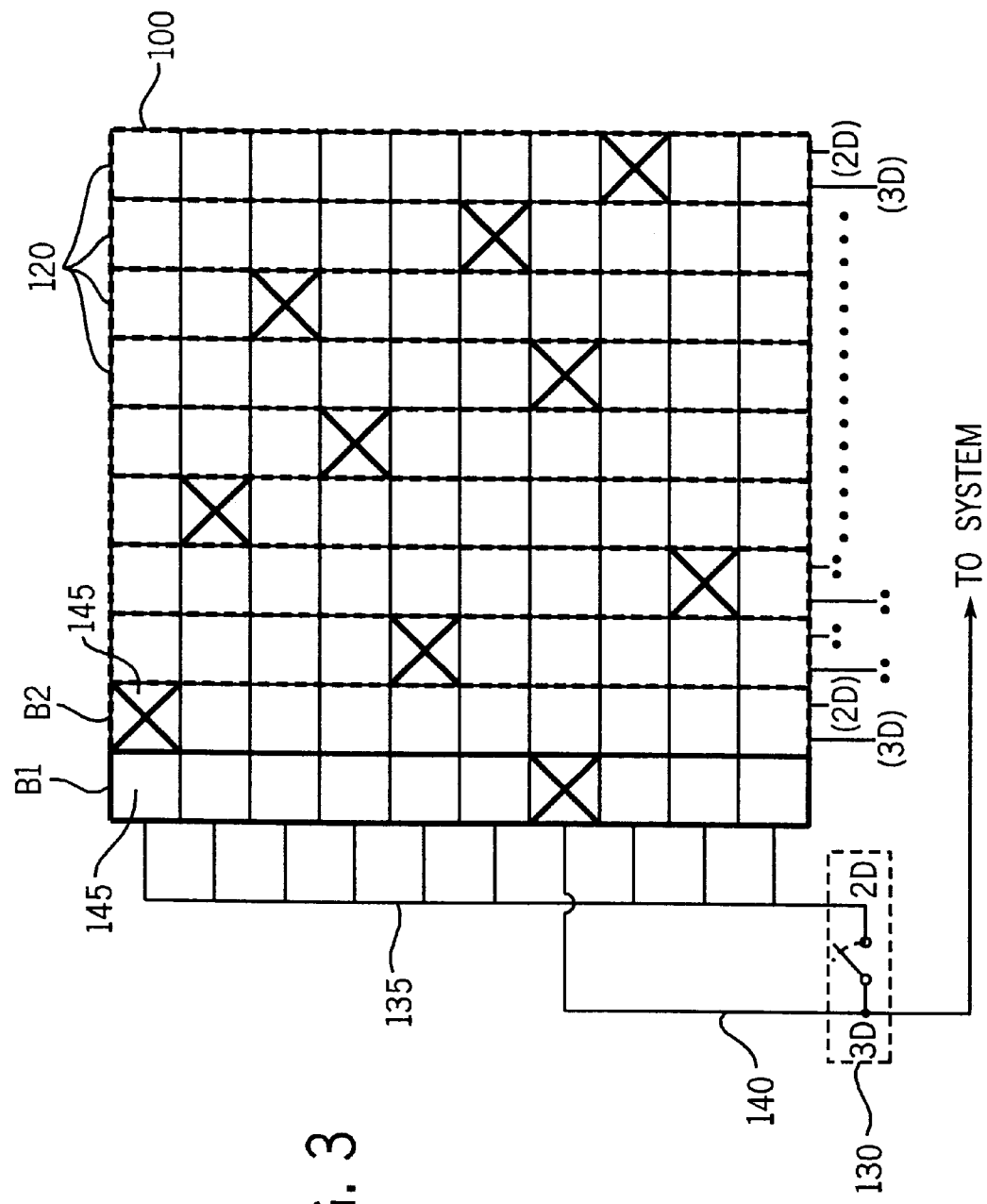
FIG. 3 illustrates the combined 2D and 3D mode operation of the two-dimensional scanning transducer array.

FIG. 3 illustrates the combined 2D and 3D mode operation of transducer array 100 which is configured to selectively operate in either a 2D and 3D mode. Additionally, FIG. 3 illustrates the 3D mode operation utilizing the same sparse binned pattern in both a transmitter and a receiver. The transducer array 100 is shown as a 10×10 array with a bin size of 1×10. However, the transducer array 100 and bin size may be of other desired dimensions in alternative embodiments.

With reference to FIG. 3, when the transducer array 100 is operating in the two-dimensional (2D) scan mode, the mode selection switch 130 is maintained in the closed position, which results in having each transducer element 105 in the bin B1 active, through lines 135 and 140. Accordingly, each transducer element 105 in bin B1 may be operatively coupled together as a fully connected array pattern, thereby transforming bin B1 into a large one-dimensional element or "super-element" 145. Similarly, other corresponding channels and switches, represented as 3D/2D ports, for each bin 120 contained in the array 100 may likewise be activated, thereby operatively transforming the series of individual bins 120, comprised of individual elements 105, into a series of large one-dimensional elements or super-elements 145. For example, bin B2, adjacent to bin B1, may be transformed from a bin 120 of individual transducer elements 105 into a super-element 145 upon the closure of the respective mode switch associated with bin B2. This process is similarly carried out for each bin 120 contained within the array 100, which transforms the array 100 into a series of large one-dimensional elements or super-elements 145, thereby operatively transforming the entire array 100 into a one-dimensional array for generating two-dimensional (2D) mages.

Alternately, when the transducer array 100 is operating in the three-dimensional (3D) scan mode utilizing the same sparse binned pattern in both the transmitter and receiver, the mode selection switch 130 is maintained in an open position, which results in having line 140 activated and line 135 deactivated. Accordingly, only transducer element #4 (transducer element #4 marked "X") would be activated, through line 140, thereby allowing transducer element #4 to generate and receive pulses used in generating a three-dimensional (3D) image. As indicated above in relation to FIG. 2, one transducer element 105 in each bin 120 is marked with an "X", such that upon the activation of line 140, the transducer element #4 (marked "X") is activated. Similarly, other corresponding transducer elements 105 marked "X" in each bin 120 may also have corresponding mode switches and channels, represented as 3D/2D ports, which may be activated in order to transform the array 100 into, sparse binned pattern array for three-dimensional (3D) imaging. In one embodiment, this process is similarly carried out for each bin contained within the array 100, to transform the transducer array 100 into sparse binned pattern array for generating three-dimensional (3D) images.

Therefore, the transducer array 100 illustrated in FIG. 3 is capable of operating in either the 2D or 3D scan mode. For each bin 120 contained within the array 100, a mode selection switch 130 is provided for switching between the two-dimensional (2D) scan mode and the three-dimensional (3D) scan mode. Therefore, when the mode switch 130 is positioned in the 2D mode (i.e.: closed position), all of the parallel coupled transducer elements 105 within a bin 120 are activated for 2D imaging. Alternately, when the mode selection switch 130 is positioned in the 3D mode (i.e.: open position), the selected active transducer elements 105 (marked "X") in each bin 120 are activated for 3D imaging. Each bin 120 contained in the array 100 has a similar switch configuration allowing the bins 120 to operate in either a 2D or 3D mode. Therefore, each bin 120 has associated switching circuitry associated with the bin 120 to allow the bin 120, and thereby the transducer array 100, to operate in either a 2D or 3D scan mode.

As shown in FIG. 3, a single 1×10 bin B1 is illustrated in detail. However, the same principles described with respect to bin B1 are equally applicable to one or more of the bins 120, having various configurations and which are contained in an array 100. When in the two-dimensional (2D) mode, all of the elements 105 in the bin 120 are coupled together to constructively form a large one-dimensional element 145 for 2D scanning. When in the three-dimensional (3D) mode, only one element (marked "X") out of the bin 120 is selected for three-dimensional (3D) scanning. As illustrated, the bin size of bin B1 is of a size 1×10, wherein element number four (marked "X"), which is shown as fourth from the bottom, has been selected for 3D imaging. The remaining 9 elements in the bin are not utilized in the three-dimensional (3D) mode. A multiplexer or other switching device (not shown) can be provided in order to realize a single mode switch 130 per bin 120. When the mode switch 130 is in the 3D position, only one of the ten elements (3D mode) within each bin 120 is coupled to the imaging system. When the switch is in the 2D position, all ten elements located within each bin 120 (2D mode) are coupled to an imaging system.

The same configuration may be repeated for all of the bins 120 in the array 100, such that, the number of mode switches 130 is equal to the number of bins 120 in the array 100. Alternatively, the different channels 125 for each bin 100 corresponding to each mode of operation may be connected to a respective mode multiplexer (not shown). Thus, in one embodiment, a selection signal can be transmitted for each different operating mode (2D or 3D) to the respective mode multiplexer, thereby activating the respective elements 105 of each bin 120 to provide a corresponding selected operating mode.

Figure 4:
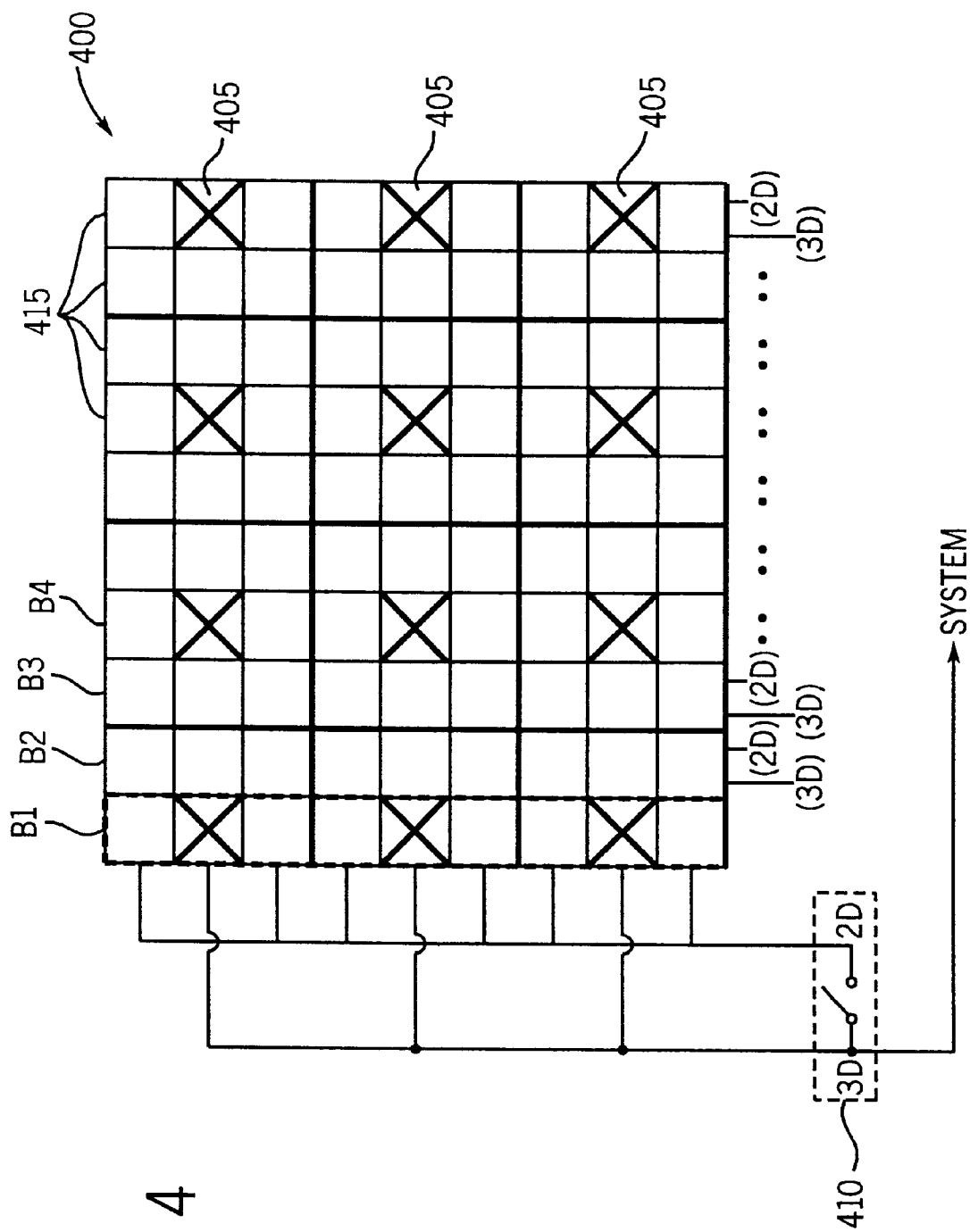
FIG. 4 is an embodiment of the two-dimensional scanning transducer array illustrating a sparse periodic pattern array.

Additionally, a sparse periodic pattern array may also be used for 3D imaging. The sparse periodic pattern array, for example as illustrated in FIG. 4, is characterized by a regular periodic pattern. In the sparse periodic pattern array 400 of FIG. 4, shown as contained within a 10×9 array divided into bin sizes of 1×9, an active transducer element 405 marked "X" is chosen out of each periodic pattern for 3D imaging. Each active transducer element 405 placement is defined by a periodicity value. For example, the transducer array 400, illustrated in FIG. 4, is configured with a periodicity value of three in both dimensions of X and Y. Usually the periodicity is the same in both dimensions. However, such a periodicity value is not required in other embodiments of the invention. Using a periodic pattern with a periodicity of three, an active transducer element 405, marked "X", is designated out of the 9 elements comprising the sparse periodic pattern to be used in three-dimensional imaging. Likewise, corresponding active transducer elements 405, marked with an "X", contained in each of the other periodicity patterns of 9 elements are used for three-dimensional imaging. As such, the sparse periodic pattern array 400 is a special case of a sparse binned array, as the periodicity patterns are equal to the product of the periodicities, which, in the present example, is 3, and the bin size is therefore nine (3×3=9). In a sparse periodic pattern, the active element 405 placement (i.e.–"X" element) is dictated by the constraints of the periodicity, since the same active elements 405 relative to the bin boundaries are connected in all of the bins.

When operating in the 3D mode, the selection mode switch 410 is maintained in the open position in order to allow the system to generate and receive pulses, from which a three-dimensional (3D) image may be generated. Upon the opening of the selection mode switch 410, three transducer elements 405 marked "X" which are contained within bin B1 are coupled to the imaging system. Therefore, upon the opening of the selection mode switch 410, three of the elements in the bin B1 are activated for 3D imaging in accordance with the sparse periodic pattern. Similarly, other bins, such as bin B4, which corresponds to the specific periodicity pattern, may have corresponding channels and switches, represented as 3D/2D ports, associated with bin B4. The channels and switches corresponding to bin B4 may likewise be activated, thereby operatively transforming the bins of individual active elements (i.e.—"X" elements) in accordance with the sparse periodic pattern for 3D imaging. This process is similarly carried out for each bin 415 contained within the array 400 to transforms the array 400 into a sparse periodic pattern array used in generating three-dimensional (3D) images.

As is apparent from FIG. 4, some of the bins 415 comprising the transducer array 400 may not have any transducer elements designated for 3D imaging, as these particular transducer elements are not within the sparse periodic pattern. For example, the bin B2 adjacent to bin B1, does not contain any transducer elements designated for 3-D imaging. Since some bins 415, such as bins B2 and B3, do not contain any active elements (marked "X") to be used for three-dimensional imaging, the corresponding mode switch and 3D imaging lines used to couple active elements (marked "X") for three-dimensional imaging may be omitted for thesse bins.

Figure 5:
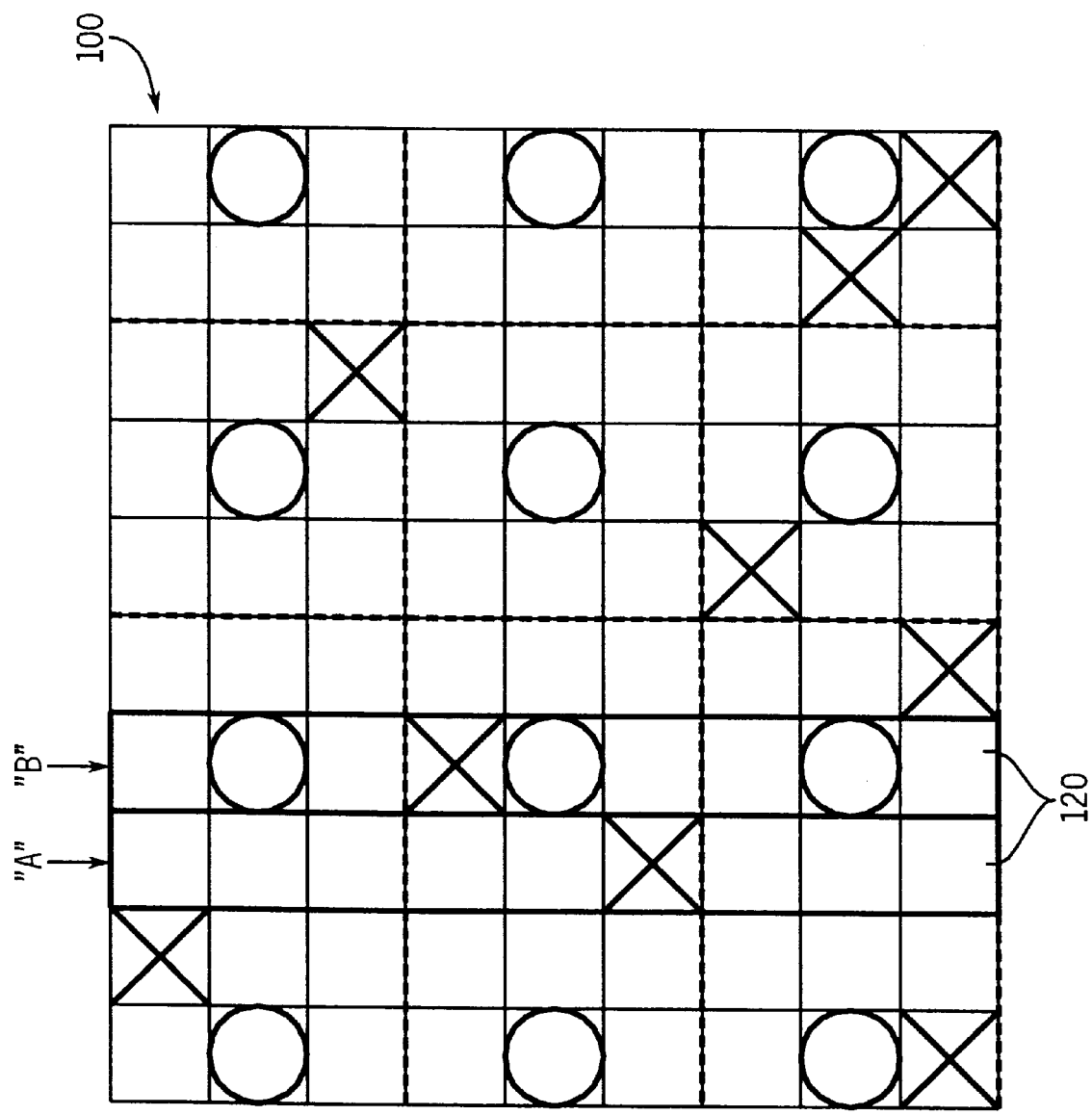
FIG. 5 illustrates the two-dimensional scanning transducer array operating in a three-dimensional (3D) scan mode.

FIG. 5 illustrates the transducer array 100 operating in a three-dimensional (3D) scan mode utilizing a sparse periodic pattern during transmission. The individual elements 105 marked with a circle "O" are arranged in a sparse periodic layout having a periodicity value of 3. The individual elements 105 marked with a circle "O" (transmitter elements) are used for transmission of pulses in the 3D mode. The individual elements 105 marked with an "X" (receiver elements) are arranged in bins 120 of size 1×9 and are used for reception in the 3D mode. The selection of elements 105 for reception may be constrained to prevent overlapping with the transmitter elements 105. Such a configuration consists of two types of bins 120, shown as bin "A" and bin "B" in FIG. 5. The "A" bin, in this example, contains only a receiver element (marked "X") and is therefore similar to the bin shown in FIG. 3, such that the switching arrangement of FIG. 3 is applicable to bin "A" without any modification. The "B" bin, however, comprises several transducer elements configured as transmitters ("O") and one element configured as a receiver ("X"). The "B" type bin may use a relatively more complex switching arrangement, as shown in FIG. 5a.

Figure 5A:
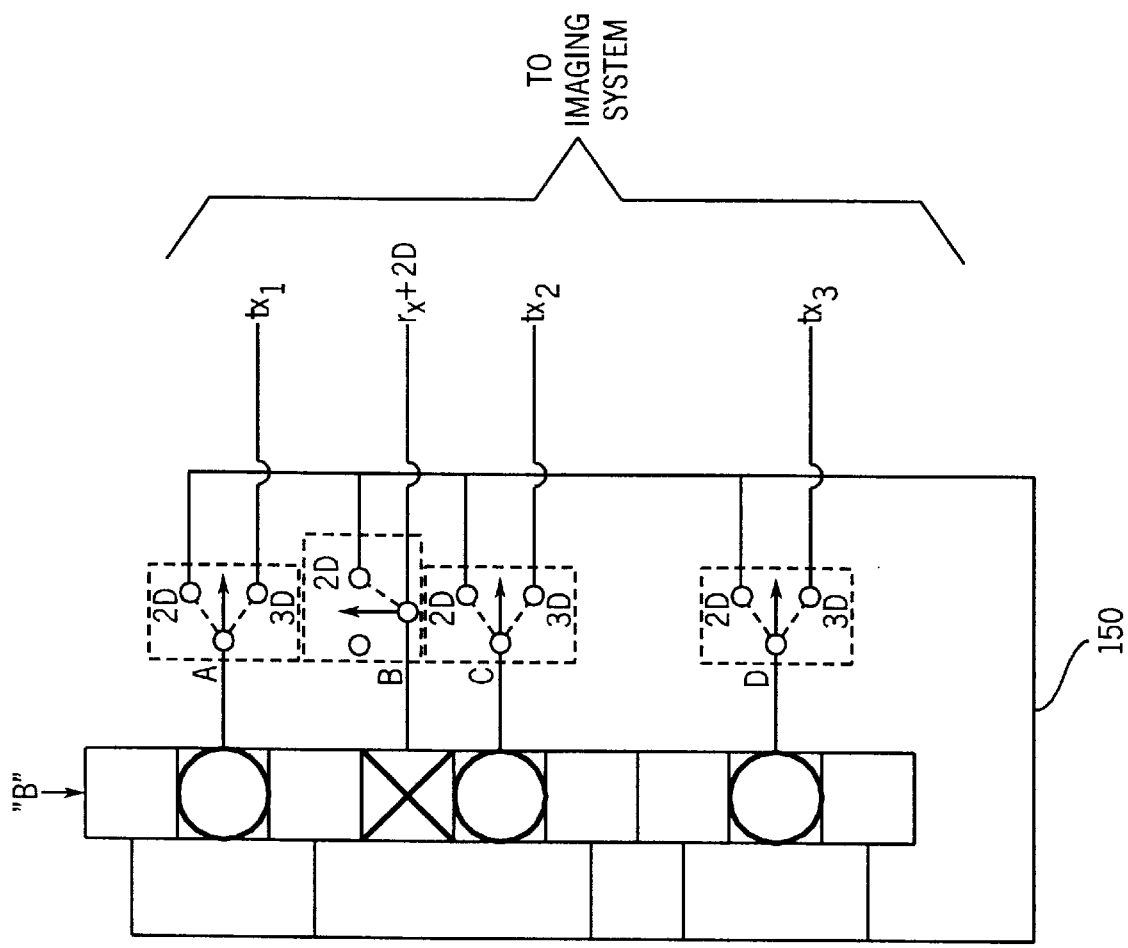
FIG. 5a illustrates an embodiment of a switching arrangement for a bin contained in the two-dimensional scanning transducer array operating in a three-dimensional (3D) scan mode.

With reference to FIG. 5a, the transducer element marked "X" in bin "B" utilizes a single switch (switch B) configuration enabling the transducer element to operate as a receiver during 3D scanning mode. During a receiving cycle, while the transducer array is operating in the 3D scanning mode, the single switch (switch B) is maintained in the open position, thereby enabling the transducer element contained in the bin to operate as a receiver. Further, while the transducer array is operating in the 2D scanning mode, the single switch (switch B) can likewise allow the transducer element marked "X", to be operated as part of a large one-dimensional element or super-element 145. Accordingly, during 2D scanning mode, switch "B" is maintained in the closed position to allow the transducer element marked "X" to operate as part of a large one-dimensional transducer element or super-element 145 through 2D line 150.

Alternatively, each transmitter element (marked "O") may use a switch with at least two positions: a 2D mode position and a 3D mode position. All the remaining elements 1, 3, 6, 7, 9 (from top to bottom) are coupled together to the 2D line 150, wherein the 2D line 150 is further coupled to an imaging system through switch B out via the rx line. Therefore the total number of single throw switches for bin "B" is one for each receiver line rx, and one double throw switch for each of the transmitter lines tx1, tx2, and tx3. This particular arrangement of switches does not depend on the transmitter elements being arranged according to a sparse periodic pattern layout, but rather may be applied to various sparse patterns wherein the receiver and transmitter elements do not overlap.

Accordingly, when operating in the two-dimensional scan mode, switches A, B, C, and D, are positioned in the 2D mode switch position during both transmission and reception of ultrasound pulses during 2D operation. The pulses are received and transmitted through the 2D line 150, wherein the 2D line 150 is coupled to an imaging system through the rx line.

When operating in the three-dimensional (3D) scan mode, switches A, C, and D are positioned in the 3D mode switch position during the transmission of ultrasound pulses during 3D operation. The pulses are supplied to the individual transmission transducer elements (marked "O"), from an associated imaging system, through transmission lines tx1, tx2, and tx3. Therefore, during a transmission cycle, the individual transmission transducer elements (marked "O") are active when operating in the 3D scanning mode. Similarly, other individual transmission transducer elements (marked "O") in other bins 120 contained in the array 100 are likewise active during transmission through similar switching arrangements.

During the reception cycle, however, switch B is maintained in an open switch position which allows for the reception of ultrasound pulses while the transducer array 100 is operating in the 3D scan mode. Accordingly, the received pulses from the transducer element(s) marked "X", while the transducer array is operating in the 3D scanning mode, are supplied to an imaging system through line $r_x$. Similarly, other individual transmission transducer elements (marked "X") in other bins 120 contained in the array 100 are likewise active during reception through similar switching arrangements.

It is understood that the imaging system allows processing ultrasound pulses from an associated transducer array as such, the present may be utilized in conjuction with various ultrasound imaging systems. Although not shown, channel multiplexers may be incorporatedin one embodiment of the present invention to allow the 2D mode signal from each super-element to be connected to both the system transmitter and the system receiver.

The invention has been described in conjunction with at least embodiment. It will be apreciated that numerous alternatives, modifications, variations and uses will be apparent to those skilled in the art in light of the foregoing description, which is not meant to be limiting on the invention, whose scope is to be defined by the following claims.

What is claimed is:

1. A device associated with a radiant pulse-echo energy imaging system, the device comprising:
   a set of bins, wherein each bin includes a set of transducer elements;
   a set of mode switches associated with the set of bins;
   wherein the set of mode switches configure the set of transducer elements in each bin to form either a one-dimensional array providing a two-dimensional scan mode or a two-dimensional array providing a three-dimensional scan mode; and
   wherein the set of transducer elements in each bin are arranged into a sparse array pattern for three-dimensional scanning.

2. The device of claim 1, wherein the set of transducer elements reside in an associated transducer assembly, and wherein the set of mode switches are integrated into the associated transducer assembly.

3. The device of claim 1, wherein each mode switch in the set of mode switches is configured to arrange the set of transducer elements in each bin to form either a one-dimensional transducer array or a two-dimensional transducer array.

4. The device of claim 1, wherein the set of transducer elements in each bin are arranged into a fully connected array pattern for two-dimensional scanning.

5. The device of claim 1, wherein the set of transducer elements in each bin use a same sparse array pattern during transmission and reception.

6. The system of claim 5, wherein the set of transducer elements in each bin uses a first sparse array pattern during transmission cycle and a second sparse array pattern during a reception cycle.

7. The device of claim 1 wherein the sparse array pattern is a periodic sparse array pattern.

8. A radiant pulse-echo energy imaging device comprising:
   pulse-echo imaging means comprising a plurality of pulse-echo elements;
   switching means associated with a defined set of pulse-echo elements;
   wherein the plurality of pulse-echo elements in each defined set of pulse-echo elements are capable of either being selectively coupled with each other to form either a one-dimensional pulse-echo imaging means configured to operate in a two-dimensional scan mode or of being operated as a two-dimensional pulse-echo imaging means configured to operate in a three dimensional scan mode; and
   wherein the defined set of pulse-echo elements are arranged into a sparse array pattern for three-dimensional scanning.

9. The device of claim 8, wherein the plurality of pulse-echo elements reside in an associated transducer assembly, and wherein the switching means are integrated into the associated transducer assembly.

10. The device of claim 8, wherein the switching means is configured to arrange the plurality of pulse-echo elements in each defined set of pulse-echo elements to form either a one-dimensional transducer array or a two-dimensional transducer array.

11. The device of claim 8, wherein the defined set of pulse-echo elements are arranged into a fully connected array pattern for two-dimensional scanning.

12. The device of claim 8, wherein the defined set of pulse-echo elements use a same sparse array pattern during transmission and reception.

13. The system of claim 12, wherein the defined set of pulse-echo elements uses a first sparse array pattern during transmission cycle and a second sparse array pattern during a reception cycle.

14. The device of claim 8 wherein the sparse array pattern is a periodic sparse array pattern.

15. A radiant pulse-echo energy imaging device comprising:
   a transducer array comprised of a plurality of transducer elements arranged into a two-dimensional transducer array;
   a first plurality of transducer elements within the two-dimensional array, wherein the first plurality of transducer elements are configured to be selectively coupled to each other to form a fully connected array pattern;
   a second plurality of transducer elements within the two-dimensional array, wherein the second plurality of transducer elements are configured to form a sparse array pattern; and
   a mode switch configured to switch operation of the two-dimensional array between the fully connected array pattern and the sparse array pattern.

16. The device of claim 15, wherein the fully connected array pattern enables the transducer array to operate in a two-dimensional scan mode.

17. The device of claim 15, wherein the fully connected array pattern of transducer elements comprises a large one dimensional transducer element.

18. The device of claim 15, wherein the sparse array pattern enables the transducer array to operate in a three-dimensional scan mode.

19. The device of claim 15, wherein transmission and reception transducer elements contained in the second plurality of transducer elements use the same sparse array pattern.

20. The device of claim 15, wherein transmission and reception transducer elements contained in the second plurality of transducer elements uses a first sparse array pattern during a transmission cycle and a second sparse array pattern during a reception cycle.

21. The device of claim 15 wherein the second plurality of transducer elements are configured to form a periodic sparse array pattern.

* * * * *